United States Patent [19]

Murata et al.

[11] Patent Number: 5,281,717
[45] Date of Patent: Jan. 25, 1994

[54] EPOXYSUCCINAMIC ACID DERIVATIVES

[75] Inventors: Mitsuo Murata, Kohnosu; Shigeyuki Sumiya, Ageo; Chihiro Yokoo, Gyoda; Katsuo Hatayama, Omiya, all of Japan

[73] Assignee: Taisho Pharmaceutical Co., Ltd., Tokyo, Japan

[21] Appl. No.: 30,089

[22] PCT Filed: Sep. 27, 1991

[86] PCT No.: PCT/JP91/01288

§ 371 Date: Mar. 1993

§ 102(e) Date: Mar. 26, 1993

[87] PCT Pub. No.: WO92/06090

PCT Pub. Date: Apr. 16, 1992

[30] Foreign Application Priority Data

Sep. 29, 1990 [JP] Japan .................. 2-261657

[51] Int. Cl.$^5$ ........................................... C07D 405/12
[52] U.S. Cl. .................................................... 548/517
[58] Field of Search ......................................... 548/517

[56] References Cited

U.S. PATENT DOCUMENTS 4,333,879 6/1982 Tamai et al. .
4,382,889 5/1983 Tamai et al. .
5,068,354 11/1991 Murata et al. .................. 548/517

FOREIGN PATENT DOCUMENTS 57-72913 5/1982 Japan .
63-275575 11/1988 Japan .
2046730 5/1983 United Kingdom .

OTHER PUBLICATIONS

Chemical Abstracts, vol. 115, No. 5, Abstract, No. 44893r; Towatori, et al. (1991).
Chemical Abstracts, vol. 115, No. 3, Abstract, No. 24916x; Murata, et al. (1991).
Agric. Giol. Chem., 42(3), 523-528 (1978), "Isolation and Characterization of E-64, A New Thiol Protease Inhibitor", Kazunori Hanada, et al, pp. 523-528.

*Primary Examiner*—Joseph Paul Brust
*Attorney, Agent, or Firm*—Oblon, Spivak, McClelland, Maier & Neustadt

[57] ABSTRACT

An epoxysuccinamic acid derivartive represented by the formula:

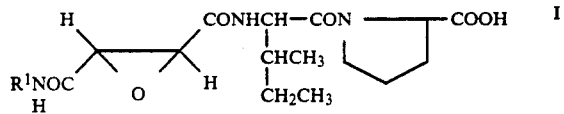

(wherein $R^1$ is an alkyl group having 1 to 10 carbon atoms, a phenyl group or a benzyl group), a pharmaceutically acceptable salt thereof, and an intermediate thereof are disclosed. The compound of Formula I is useful as a therapeutic agent for muscular atrophy diseases.

4 Claims, No Drawings

EPOXYSUCCINAMIC ACID DERIVATIVES

TECHNICAL FIELD

The present invention relates to epoxysuccinamic acid derivatives useful as medicines, and more particularly to epoxysuccinamic acid derivatives inhibiting cathepsin B specifically, and the preparation intermediates thereof.

BACKGROUND ART

Calcium-activated neutral protease (CANP), cathepsin B and cathepsin L, each of which belongs to cysteine proteases, are considered to be associated with the decomposition of muscular structure protein in malignant muscular atrophy diseases such as muscular dystrophy and distal myopathy.

Some epoxysuccinic acid derivatives such as N-(L-3-trans-carboxyoxirane-2-carbonyl)-L-leucylagmatine [Agric. Biol. Chem., vol. 42, pp. 523-528 (1978)], epoxysuccinyl dipeptide derivatives (U.K. Patent No. 2,046,730) and the like have been heretofore known as the compound inhibiting several thiol proteases. However, no epoxysuccinic acid derivatives inhibiting specifically only one of the cysteine proteases have been known.

As a result of the earnest research to compounds having an epoxy ring, the present inventors have found the compounds inhibiting cathepsin B ally unlike the known compounds, and have accomplished the present invention.

DISCLOSURE OF THE INVENTION

The present invention is an epoxysuccinamic acid derivative represented by Formula I:

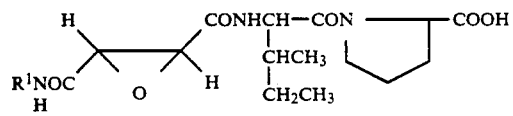

(wherein $R^1$ is an alkyl group having 1 to 10 carbon atoms, a phenyl group or a benzyl group) and a pharmaceutically acceptable salt thereof.

In addition, the present invention is an epoxysuccinamic acid derivative represented by Formula II:

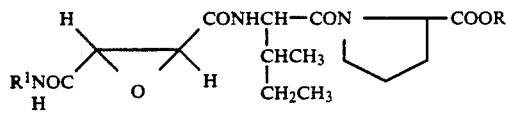

(wherein $R^1$ is as defined above, $R^2$ is a protecting group of the carboxyl group), which is a preparation intermediate of the compound of Formula I.

In the present invention, the alkyl group having 1 to 10 carbon atoms refers to a straight chain, branched chain or cyclic alkyl group such as, for example, a methyl group, an ethyl group, an n-propyl group, an n-butyl group, an n-pentyl group, an isopropyl group, an isobutyl group, a t-butyl group and a cyclohexyl group, and preferably an n-propyl group and an n-pentyl group. The protecting group of the carboxyl group refers to those used usually in the field of the peptide synthesis chemistry, for example, a benzyl group, a p-methoxybenzyl group, a p-nitrobenzyl group, a t-butyl group, a benzhydryl group, a trimethylsilyl group, a methyl group and an ethyl group.

The pharmaceutically acceptable salts of the present invention are salts with inorganic bases including sodium, potassium, magnesium, ammonium and the like, salts with organic bases or basic amino acids (e.g. triethylamine, cyclohexylamine, arginine and lysine), salts with mineral acids (e.g. sulfuric acid, hydrochloric acid and phosphoric acid), salts with organic acids and acidic amino acids (e.g. acetic acid, lactic acid, tartaric acid, fumaric acid, maleic acid, glutamic acid and aspartic acid).

The compounds of the present invention can be prepared, for example, by the following processes (in the following formulae, $R^1$ and $R^2$ are as defined above, and $R^2$ and $R^3$ may be the same or different, and each of which is a protecting group of the carboxyl group).

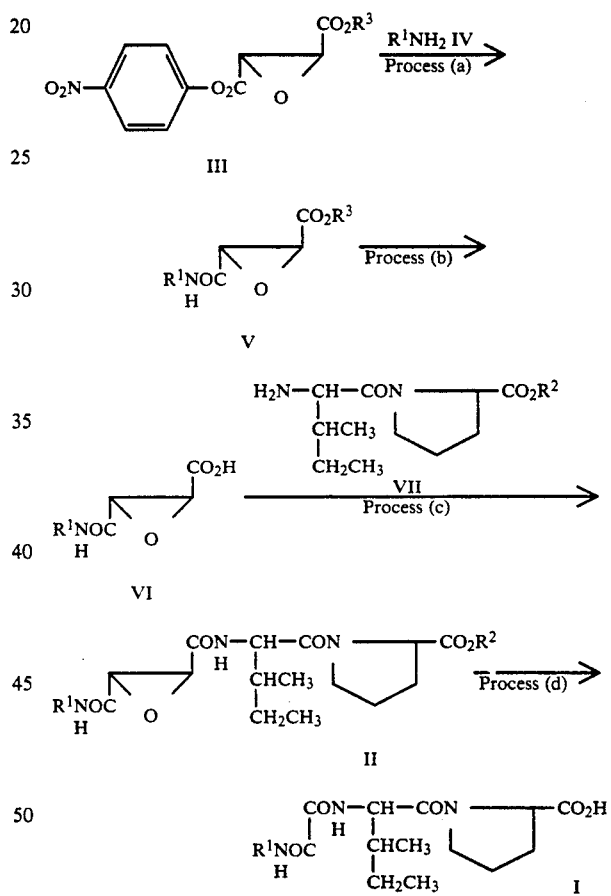

Process (a): An epoxysuccinic acid derivative of Formula III which can be prepared according to the method described in Chem. Pharm. Bull., vol. 35, pp. 1098-1104 (1987), is reacted with 1.0-2.0 molar equivalents of an amine of Formula IV in a solvent such as chloroform, ethyl acetate and N,N-dimethylformamide to give a compound of Formula V.

Process (b): The protecting group of the carboxyl group of the compound of formula V is removed in a solvent such as methanol, ethanol and N,N-dimethylformamide according to a method and conditions used usually in the field of the peptide synthesis chemistry such as a catalytic reduction using a catalyst such as palladium carbon and palladium black, a catalytic transfer hydrogenation (CTH) or hydrolysis using an acid (e.g. trifluoroacetic acid, methanesulfonic acid, hydrobromic acid and hydrochloric acid) or a base (e.g. sodium hydroxide and potassium hydroxide) to give a compound of Formula VI.

Process (c): A dipeptide derivative of Formula VII, which can be prepared by using isoleucine and proline according to a method used usually in the field of the peptide synthesis chemistry, is condensed with 1.0-2.0 molar equivalents of a compound of Formula VI in a solvent such as chloroform, ethyl acetate and N,N-dimethylformamide according to a method and conditions used usually in the field of the peptide synthesis chemistry such as a method using a carbodiimide compound (e.g. N,N'-dicyclohexylcarbodiimide and N-ethyl-N'-(3-dimethylaminopropyl)carbodiimide hydrochloride), a mixed anhydride method, a acid halide method, an azide method and an activated ester method to give a compound of Formula II of the present invention.

Process (d): The protecting group of a carboxyl group of the compound of Formula II is removed by the same method and conditions as used in Process (b) to give a compound of Formula I of the present invention.

Furthermore, the amine of Formula IV and the dipeptide derivative of Formula VII may be each used in the form of a salt such as salts with hydrochloric acid, sulfuric acid and p-toluenesulfonic acid. In this case, the reaction may be carried out in the presence of a base such as triethylamine, N,N-diisopropylethylamine, N-methylmorpholine and pyridine.

The compounds of Formula I thus obtained hardly inhibit papain and CANP which belong to cysteine proteases, but strongly inhibit cathepsin B specifically.

The experiments are shown below.

EXPERIMENTS

The inhibitory activities against papain, CANP and cathepsin B were measured according to the following methods, and results are shown in Table 1.

EXPERIMENT 1

Inhibitory Activity Against Papain

The measurement was carried out according to the method of A. J. Barrett et al [Biochem. J., vol. 201, p. 189 (1982)].

To each of 0.95 ml of the reaction solutions containing 2.5 mM 2-mercaptoethanol, 1 mM disodium ethylenediaminetetraacetate, 0.1 M sodium potassium phosphate buffer (pH 6.8), 0.1% Brij-35 (produced by Nacalai Tesque Inc.), 1% dimethyl sulfoxide and various concentrations of the test drug was added 25 μl of a papain solution (produced by Sigma Chemical Co.), and the mixture was preincubated at 40° C. for 3 minutes, after which 25 μl of 200 μM benzyloxycarbonyl-L-phenylalanyl-L-arginine 4-methylcoumaryl-7-amide (produced by Peptide Institute Inc.) was added for starting the reaction After incubation at 40° C. for 10 minutes, the reaction was stopped by addition of 1 ml of 100 mM sodium acetate buffer solution (pH 4.3) containing 100 mM sodium chloroacetate. The fluorescence of the liberated 7-amino-4-methylcoumarine was determined using a Shimazu fluorometer RF-5000 with excitation at 380 nm and emission measured at 440 nm. The concentration of the test drug required for 50% inhibition (IC$_{50}$) was calculated from the inhibition rate calculated using the value which was measured in a similar manner to the above but without the test drug.

EXPERIMENT 2

Inhibitory Activity Against CANP

The measurement was carried out according to the method of S. Ishiura et al (J. Biochem., vol. 84, p. 225 (1978)].

Each of 0.45 ml of the reaction solutions containing 25 mM 2-mercaptoethanol, 5 mM calcium chloride, 0.1 M sodium glycerophosphate-HCl buffer (pH 7.5), 0.24% alkali-denatured casein, 1% dimethylsulfoxide and various concentrations of the test drug was preincubated accurately at 30° C. for 5 minutes, and 50 μl of a solution containing 5 μg of μ CANP (Calpain I, produced by Nacalai Tesque Inc.) was added for starting the reaction. After exact incubation at 30° C. for 20 minutes, the reaction was stopped by addition of 0.5 ml of 10% trichloroacetic acid. After being allowed to stand at room temperature for 60 minutes, the mixture was centrifuged at 3000 × g for 5 minutes, and the absorbance at 280 nm of the supernatant was determined. The remaining activity was obtained by reducing the blank value which was obtained in a similar manner to the above but adding 10% trichloroacetic acid prior to addition of μ CANP from the above value. The concentration of the test drug required for 50% inhibition (IC$_{50}$) was calculated from the inhibition rate obtained using the value which was measured in a similar manner to the above but without the test drug.

EXPERIMENT 3

Inhibitory Activity against Cathepsin B

The measurement was carried out according to the method of A. J. Barrett et al [Biochem. J., vol. 201, page 189 (1982)].

To each of 0.95 ml of the reaction solutions containing 2.5 mM 2-mercaptoethanol, 1 mM disodium ethylenediaminetetraacetate, 0.1 M sodium potassium phosphate buffer (pH 6.0), 0.1% Brij-35 (produced by Nacalai Tesque Inc.), 1% dimethyl sulfoxide and various concentrations of the test drug was added 25 μl of 200 nM cathepsin B solution (produced by Sigma Chemical Co.), and the mixture was preincubated at 40° C. for 3 minutes, after which 25 μl of 200 μM benzyloxycarbonyl-L-phenylalanyl-L-arginine 4-methylcoumaryl-7-amide (produced by Peptide Institute Inc.) was added for starting the reaction After incubation at 40° C. for 10 minutes, the reaction was stopped by addition of 1 ml of 100 mM sodium acetate buffer (pH 4.3) containing 100 nM sodium chloroacetate. The fluorescence of the liberated 7-amino-4-methyl-coumarine was determined using a Shimazu fluorometer RP-5000 with excitation at 380 nm and emission measured at 440 nm. The concentration of the test drug required for 50% inhibition (IC$_{50}$) was calculated from the inhibiting rate calculated using the value which was measured in a similar manner to the above but without the test drug.

TABLE 1

| Test drug (Compound No.) | Inhibitory Activity Value [IC$_{50}$ (nM)] | | |
|---|---|---|---|
| | Papain | CANP | Cathepsin B |
| 1d | 57,400 | >200,000 | 42 |

TABLE 1-continued

| | Inhibitory Activity Value [IC$_{50}$ (nM)] | | |
|---|---|---|---|
| Test drug (Compound No.) | Papain | CANP | Cathepsin B |
| 8d | 26,000 | >200,000 | 32 |

(Note)
The test drugs in the table are the compounds which are obtained in the following examples.

BEST MODE FOR CARRYING OUT THE INVENTION

The present invention is hereinafter illustrated in more detail by the following examples.

EXAMPLE 1

(a) To a solution of 2.0 g (5.8 mM) of L-trans-epoxysuccinic acid benzyl p-nitrophenyl ester in 13 ml of ethyl acetate was added dropwise a solution of 413 mg (7.0 mM) of n-propylamine in 2 ml of ethyl acetate under ice cooling with stirring and further stirring was continued under ice cooling for an hour and at room temperature overnight. Then, 85 ml of ethyl acetate was added, and the mixture was washed successively with 100 ml each of 1N ammonia water, water, 5% aqueous hydrochloric acid solution, water and a saturated aqueous sodium chloride solution. The organic layer was dried over anhydrous magnesium sulfate, filtered and evaporated under reduced pressure. The residue was chromatographed on a silica gel column (eluent; ethyl acetate : n-hexane =1:2) to give 1.08 g of L-3-trans-n-propyl-carbamoyloxirane-2-carboxylic acid benzyl ester.

NMR (DMSO-d$_6$) δ(ppm);
0.83(3H, t, J=7.3Hz),
1.43(3H, tq, J=7.3, 7.3Hz),
3.05(2H, dt, J=5.4, 7.3Hz),
3.63(1H, d, J=1.8Hz), 3.68(1H, d, J=1.8Hz),
5.20(2H,s), 7.39(5H, s),
8.39(1H, t, J=5.4Hz)
IR $\nu_{max}^{KBr}$ cm$^{-1}$;
3284, 1749, 1661, 1568, 1346, 1282, 1233, 1208, 898

(b) To a suspension of 20 mg of 10% palladium carbon in 20 ml of methanol was added 851 mg (3.2 mM) of L-3-trans-n-propylcarbamoyloxirane-2-carboxylic acid benzyl ester, and stirring was continued under a hydrogen atmosphere for 2 hours The palladium carbon was filtered off, and washed with methanol The filtrate and the washings were combined and evaporated under reduced pressure to give 550 mg of L-3-trans-n-propyl-carbamoyloxirane-2-carboxylic acid.

NMR (DMSO-d$_6$) δ(ppm);
0.84(3H, t, J=7.3Hz),
1.43(2H, tq, J=7.3, 7.3Hz),
3.06(2H, dt, J=5.4, 7.3Hz),
3.46(1H, d, J=1.8Hz), 3.53(1H, d, J=1.8Hz),
8.34(1H, t, J=5.4Hz),
12.50~14.35(1H, broad)
IR $\nu_{max}^{KB4}$ cm$^{-1}$;
3318, 2964, 1768, 1651, 1582, 1455, 1382, 1348, 1274, 1242, 1220, 1151, 984, 894

(c) To a solution of 500 mg (2.9 mM) of L-3-trans-n-propylcarbamoyloxirane-2-carboxylic acid, 1.04 g (2.9 mM) of L-isoleucyl-L-proline benzyl ester hydrochloride, 365 mg (3.2 mM) of N-hydroxysuccinimide and 609 mg (3.2 mM) of 1-ethyl-3-(3-dimethylaminopropyl)-carbodiimide hydrochloride in 13 ml of N,N-dimethylformamide was added dropwise a solution of 293 mg (2.9 mM) of N-methylmorpholine in 2 ml of N,N-dimethylformamide under ice cooling with stirring, and further stirring was continued under ice cooling for an hour and at room temperature overnight. To the reaction mixture was added 150 ml of a mixture of ethyl acetate and benzene (4:1), and the mixture was washed successively with 150 ml each of 5% aqueous hydrochloric acid solution, water, a saturated aqueous sodium bicarbonate solution, water and a saturated aqueous sodium chloride solution The organic layer was dried over anhydrous magnesium sulfate, filtered and evaporated under reduced pressure The residue was chromatographed on a silica gel column (eluent; ethyl acetate n-hexane =4:1) to give 830 mg of N-(L-3-trans-n-propylcarbamoyloxirane-2-carbonyl)-L-isoleucyl-L-proline benzyl ester.

NMR (DMSO-d$_6$) δ(ppm);
0.72~0.90 (9H, m), 0.96~1.22(1H, m),
1.36~1.56(1H, m),
1.42(2H, tq, J=7.3, 7.3Hz),
1 65~2.00(4H, m), 2.10~2.28(1H, m),
2.94~3.12(2H, m), 3.47(1H, d, J=1.8Hz),
3.52~3.85(2H, m), 3.65(1H, d, J=1.8Hz),
4.35~4.49(2H, m), 5.12(2H, s), 7.36(5H, s),
8.32(1H, t, J=5.7Hz), 8.75(1H, d, J=8.4Hz)
IR $\nu_{max}^{CHCl_3}$ cm$^{-1}$;
2969, 1742, 1685, 1645, 1520, 1447, 1276, 1238, 1174, 898
MS (FAB); m/z:474(M+)

(d) To a suspension of 20 mg of 10% palladium carbon in 20 ml of methanol was added 690 mg (1.5 mM) of N-(L-3-trans-n-propylcarbamoyloxirane-2-carbonyl)-L-isoleucyl-L-proline benzyl ester, and stirring was continued under a hydrogen atmosphere for an hour. The palladium carbon was filtered off, and washed with methanol. The filtrate and washings were combined and evaporated under reduced pressure to give 500 mg of N-(L-3-trans-n-propylcarbamoyloxirane-2-carbonyl)-L-isoleucyl-L-proline (Compound 1d).

NMR (DMSO-d$_6$) δ(ppm);
0.84(6H, t, J=7.3Hz), 0.92(3H, d, J=6.8Hz),
0.96~1.20(1H, m), 1.38 .1.58(1H, m),
1.42(2H, tq, J=7.3, 7.3Hz),
1.67~2.01(4H, m), 2.05~2.21(1H, m),
2.95~3.14(2H, m), 3.48(1H, d, J=1.8Hz),
3.50~3.83(2H, m), 3.65(1H, d, J=1.8Hz),
4.20~4.30(1H, m),
4.42(1H, dd, J=8,5, 8.5Hz),
8.32(1H, t, J=5.7Hz), 8.72(1H, d, J=8.5Hz),
12.00~13.20(1H, broad)
IR $\nu_{max}^{KBr}$ cm$^{-1}$;
3285, 2969, 1733, 1630, 1546, 1452, 1324, 1228, 1193, 1049, 898
MS (FAB); m/z: 384(MH+)

Following the procedure and reaction condition disclosed in Example 1a using ethylamine, isopropylamine, t-butylamine, isobutylamine, n-butylamine, isoamylamine, n-amylamine, n-hexylamine, n-heptylamine, benzylamine, aniline or cyclohexylamine in place of n-propylamine, there were obtained the compounds shown in Table 2.

TABLE 2

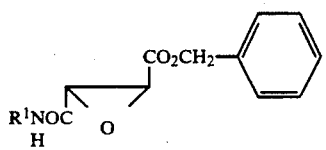

| Compound No. | $R^1$ | NMR (DMSO-$d_6$) δ(ppm) | IR(cm$^{-1}$) |
|---|---|---|---|
| 2a | $CH_3CH_2-$ | 1.14(3H, t, J=7.3Hz)<br>3.21~3.38(2H, m)<br>3.51(1H, d, J=1.9Hz)<br>3.69(1H, d, J=1.9Hz)<br>5.17(1H, d, J=12.1Hz)<br>5.26(1H, d, J=12.1Hz)<br>5.90~6.15(1H, broad)<br>7.37(5H, s) | (KBr)<br>3286<br>1748<br>1656<br>1572<br>1384<br>1340<br>1275<br>1233<br>1207<br>894 |
| 3a | $(CH_3)_2CH-$ | 1.12(3H, d, J=6.6Hz)<br>1.17(3H, d, J=6.6Hz)<br>3.49(1H, d, J=1.9Hz)<br>3.67(1H, d, J=1.9Hz)<br>3.93~4.18(1H, m)<br>5.17(1H, d, J=12.1Hz)<br>5.26(1H, d, J=12.1Hz)<br>5.75~5.95(1H, broad)<br>7.37(5H, s) | (KBr)<br>3286<br>1749<br>1656<br>1561<br>1352<br>1268<br>1232<br>1206<br>898 |
| 4a | $(CH_3)_3C-$ | 1.27(9H, s)<br>3.63(1H, d, J=1.9Hz)<br>3.64(1H, d, J=1.9Hz)<br>5.16(1H, d, J=12.3Hz)<br>5.23(1H, d, J=12.3Hz)<br>7.28~7.53(5H, m)<br>8.08(1H, bs) | 3306 (neat)<br>2971<br>1752<br>1668<br>1551<br>1457<br>1366<br>1279<br>1217<br>1192<br>1003<br>897 |
| 5a | $(CH_3)_2CHCH_2-$ | 0.84(6H, d, J=6.7Hz)<br>1.70(1H, tqq, J=6.7, 6.7, 6.7Hz)<br>2.93(2H, ddd, J=6.7, 5.8, 1.0Hz)<br>3.67(1H, d, J=1.8Hz)<br>3.68(1H, d, J=1.8Hz)<br>5.17(1H, d, J=12.4Hz)<br>5.24(1H, d, J=12.4Hz)<br>7.40(5H, s)<br>8.42(1H, t, J=5.8Hz) | 3274 (KBr)<br>1749<br>1685<br>1576<br>1455<br>1382<br>1339<br>1268<br>1233<br>1206<br>1164<br>988<br>893 |
| 6a | $CH_3(CH_2)_3-$ | 0.87(3H, t, J=7.1Hz)<br>1.14~1.49(4H, m)<br>3.09(2H, dt, J=5.6, 6.6Hz)<br>3.63(1H, d, J=1.8Hz)<br>3.68(1H, d, J=1.8Hz)<br>5.18(1H, d, J=12.8Hz)<br>5.24(1H, d, J=12.8Hz)<br>7.40(5H, s)<br>8.39(1H, t, J=5.6Hz) | 3287 (KBr)<br>1751<br>1657<br>1558<br>1347<br>1276<br>1256<br>1230<br>1208<br>896 |
| 7a | $(CH_3)_2CH(CH_2)_2-$ | 0.86(6H, d, J=6.6Hz)<br>1.31(2H, dt, 6.8, 7.1Hz)<br>1.56(1H, tqq, J=6.8, 6.6, 6.6Hz)<br>3.11(2H, dt, J=5.3, 7.1Hz)<br>3.62(1H, d, J=1.9Hz)<br>3.67(1H, d, J=1.9Hz)<br>5.21(2H, s)<br>7.40(5H, s)<br>8.36(1H, t, J=5.3Hz) | (KBr)<br>3276<br>1748<br>1665<br>1575<br>1458<br>1385<br>1347<br>1278<br>1235<br>1203<br>895 |
| 8a | $CH_3(CH_2)_4-$ | 0.86(3H, t, J=6.7Hz)<br>1.12~1.52(6H, m)<br>3.01~3.15(2H, m)<br>3.62(1H, d, J=1.8Hz) | 3317 (KBr)<br>2927<br>1749<br>1655 |

TABLE 2-continued

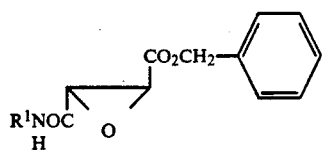

| Compound No. | $R^1$ | NMR (DMSO-$d_6$) δ(ppm) | IR(cm$^{-1}$) |
|---|---|---|---|
| | | 3.68(1H, d, J=1.8Hz) | 1573 |
| | | 5.17(1H, d, J=12.7Hz) | 1458 |
| | | 5.24(1H, d, J=12.7Hz) | 1375 |
| | | 7.40(5H, s) | 1342 |
| | | 8.39(1H, t, J=5.6Hz) | 1264 |
| | | | 1231 |
| | | | 1188 |
| | | | 968 |
| | | | 900 |
| 9a | $CH_3(CH_2)_5$— | 0.86(3H, t, J=6.5Hz) | 3285 (KBr) |
| | | 1.14~1.50(8H, m) | 2926 |
| | | 3.08(2H, dt, J=5.5, 6.5Hz) | 1750 |
| | | 3.62(1H, d, J=1.8Hz) | 1737 |
| | | 3.67(1H, d, J=1.8Hz) | 1661 |
| | | 5.20(2H, s) | 1568 |
| | | 7.39(5H, s) | 1456 |
| | | 8.39(1H, t, J=5.5Hz) | 1379 |
| | | | 1343 |
| | | | 1293 |
| | | | 1280 |
| | | | 1198 |
| | | | 1022 |
| | | | 974 |
| | | | 897 |
| 10a | $CH_3(CH_2)_6$— | 0.85(3H, t, J=6.5Hz) | 3322 (KBr) |
| | | 1.10~1.52(10H, m) | 2925 |
| | | 3.08(2H, dt, J=5.4, 6.5Hz) | 1747 |
| | | 3.62(1H, d, J=1.8Hz) | 1651 |
| | | 3.67(1H, d, J=1.8Hz) | 1566 |
| | | 5.20(2H, s) | 1469 |
| | | 7.39(5H, s) | 1378 |
| | | 8.38(1H, t, J=5.4Hz) | 1343 |
| | | | 1258 |
| | | | 1231 |
| | | | 1196 |
| | | | 982 |
| | | | 900 |
| 11a | $PhCH_2$— | 3.71(1H, d, J=1.8Hz) | 3288 (KBr) |
| | | 3.74(1H, d, J=1.8Hz) | 1747 |
| | | 4.31(2H, d, J=5.8Hz) | 1656 |
| | | 5.17(1H, d, J=12.4Hz) | 1562 |
| | | 5.24(1H, d, J=12.4Hz) | 1456 |
| | | 7.17~7.50(10H, m) | 1342 |
| | | 8.93(1H, t, J=5.8Hz) | 1264 |
| | | | 1232 |
| | | | 1191 |
| | | | 902 |
| 12a | Ph— | 3.83(1H, d, J=1.8Hz) | 3263 (KBr) |
| | | 3.87(1H, d, J=1.8Hz) | 3066 |
| | | 5.23(2H, s) | 1750 |
| | | 7.05~7.16(1H, m) | 1669 |
| | | 7.27~7.47(7H, m) | 1547 |
| | | 7.56~7.67(2H, m) | 1345 |
| | | 10.48(1H, bs) | 1234 |
| | | | 1207 |
| | | | 896 |
| 13a | $C_6H_{11}$— | 1.05-1.80(10H, m) | 3278 (KBr) |
| | | 3.45~3.65(1H, m) | 2928 |
| | | 3.63(1H, d, J=1.8Hz) | 1749 |
| | | 3.67(1H, d, J=1.8Hz) | 1659 |
| | | 5.18(1H, d, J=12.3Hz) | 1562 |
| | | 5.24(1H, d, J=12.3Hz) | 1345 |
| | | 7.40(5H, s) | 1227 |
| | | 8.34(1H, d, J=7.9Hz) | 1204 |
| | | | 897 |

Following the procedure and reaction conditions disclosed in Example 1b using Compounds 2a-13 a in Table 2, there were obtained the corresponding compounds shown in Table 3.

TABLE 3

$$R^1NOC-CH(-CO_2H)-O-$$ (with H on N)

| Compound No. | $R^1$ | NMR (DMSO-$d_6$) δ(ppm) | IR(cm$^{-1}$) |
|---|---|---|---|
| 2b | $CH_3CH_2-$ | 1.03(3H, t, J=7.2Hz)<br>3.12(2H, dq, J=5.5, 7.2Hz)<br>3.47(1H, d, J=1.8Hz)<br>3.51(1H, d, J=1.8Hz)<br>8.35(1H, t, J=5.5Hz)<br>13.25~13.70(1H, broad) | 3320 (KBr)<br>2979<br>1769<br>1651<br>1579<br>1382<br>1362<br>894 |
| 3b | $(CH_3)_2CH-$ | 1.07(6H, d, J=6.6Hz)<br>3.46(1H, d, J=1.8Hz)<br>3.50(1H, d, J=1.8Hz)<br>3.75~3.98(1H, m)<br>8.27(1H, d, J=7.3Hz)<br>12.90~13.90(1H, broad) | 3333 (Neat)<br>2978<br>1742<br>1662<br>1556<br>1454<br>1235<br>897 |
| 4b | $(CH_3)_3C-$ | 1.27(9H, s)<br>3.43(1H, d, J=1.8Hz)<br>3.54(1H, d, J=1.8Hz)<br>8.02(1H, bs)<br>13.05~13.75(1H, broad) | 3347 (KBr)<br>2978<br>1737<br>1646<br>1563<br>1458<br>1395<br>1367<br>1328<br>1284<br>1216<br>894 |
| 5b | $(CH_3)_2CHCH_2-$ | 0.84(6H, d, J=6.6Hz)<br>1.71(1H, tqq, J=6.4, 6.6, 6.6Hz)<br>2.93(2H, dd, J=5.5, 6.4Hz)<br>3.46(1H, d, J=1.9Hz)<br>3.57(1H, d, J=1.9Hz)<br>8.36(1H, t, J=5.5Hz)<br>13.20~13.75(1H, broad) | 3310 (KBr)<br>1733<br>1645<br>1563<br>1474<br>1326<br>1269<br>1230<br>993<br>892 |
| 6b | $CH_3(CH_2)_3-$ | 0.87(3H, t, J=7.0Hz)<br>1.17~1.50(4H, m)<br>3.09(2H, dt, J=5.5, 6.4Hz)<br>3.46(1H, d, J=1.9Hz)<br>3.53(1H, d, J=1.9Hz)<br>8.33(1H, t, J=5.5Hz)<br>13.46(1H, bs) | 3335 (KBr)<br>3277<br>2962<br>1742<br>1662<br>1574<br>1454<br>1385<br>1313<br>1242<br>892 |
| 7b | $(CH_3)_2CH(CH_2)_2-$ | 0.87(6H, d, J=6.6Hz)<br>1.31(2H, dt, J=6.8, 7.5Hz)<br>1.57(1H, tqq, J=6.8, 6.6, 6.6Hz)<br>3.11(2H, dt, J=5.5, 7.5Hz)<br>3.45(1H, d, J=1.9Hz)<br>3.52(1H, d, J=1.9Hz)<br>8.31(1H, t, J=5.5Hz)<br>13.20~13.75(1H, broad) | 3335 (KBr)<br>3273<br>2960<br>1742<br>1661<br>1576<br>1454<br>1386<br>1311<br>1242<br>892 |
| 8b | $CH_3(CH_2)_4-$ | 0.86(3H, t, J=6.7Hz)<br>1.12~1.55(6H, m)<br>3.08(2H, dt, J=5.5, 6.7Hz)<br>3.46(1H, d, J=1.8Hz)<br>3.53(1H, d, J=1.8Hz)<br>8.34(1H, t, J=5.5Hz)<br>13.25~13.65(1H, broad) | 3339 (KBr)<br>3267<br>2952<br>2863<br>1742<br>1719<br>1661<br>1627<br>1577<br>1456<br>1397<br>1281<br>1242<br>1193<br>895 |

TABLE 3-continued $$R^1NOC\underset{H}{\overset{CO_2H}{\diagup\diagdown}}O$$

| Compound No. | $R^1$ | NMR (DMSO-$d_6$) δ(ppm) | IR(cm$^{-1}$) |
|---|---|---|---|
| 9b | $CH_3(CH_2)_5-$ | 0.86(3H, t, J=6.5Hz)<br>1.13~1.50(8H, m)<br>3.08(2H, dt, J=5.5, 6.5Hz)<br>3.45(1H, d, J=1.8Hz)<br>3.52(1H, d, J=1.8Hz)<br>8.33(1H, t, J=5.5Hz)<br>13.25~13.60(1H, broad) | 3337 (KBr)<br>3264<br>2957<br>2930<br>1742<br>1724<br>1661<br>1631<br>1579<br>1455<br>1397<br>1242<br>1191<br>894 |
| 10b | $CH_3(CH_2)_6-$ | 0.86(3H, t, J=6.5Hz)<br>1.12~1.55(10H, m)<br>3.08(2H, dt, J=5.5, 6.5Hz)<br>3.45(1H, d, J=1.9Hz)<br>3.52(1H, d, J=1.9Hz)<br>8.32(1H, t, J=5.5Hz)<br>13.30~13.60(1H, broad) | 3259 (KBr)<br>2921<br>1734<br>1693<br>1662<br>1576<br>1465<br>1392<br>1262<br>1225<br>888 |
| 11b | $PhCH_2-$ | 3.52(1H, d, J=1.8Hz)<br>3.61(1H, d, J=1.8Hz)<br>4.32(2H, d, J=5.9Hz)<br>7.19~7.39(5H, m)<br>8.89(1H, t, J=5.9Hz)<br>13.10~13.80(1H, broad) | 3294 (KBr)<br>1745<br>1665<br>1568<br>1455<br>1388<br>1263<br>1239<br>891 |
| 12b | $Ph-$ | 3.62(1H, d, J=1.8Hz)<br>3.78(1H, d, J=1.8Hz)<br>7.02~7.19(1H, m)<br>7.25~7.43(2H, m)<br>7.55~7.68(2H, m)<br>10.42(1H, bs)<br>13.00~14.00(1H, broad) | 3353 (KBr)<br>3270<br>1752<br>1731<br>1675<br>1605<br>1551<br>1446<br>1216<br>903 |
| 13b | $C_6H_{11}-$ | 1.00~1.90(10H, m)<br>3.41~3.68(1H, m)<br>3.45(1H, d, J=1.9Hz)<br>3.53(1H, d, J=1.9Hz)<br>8.29(1H, d, J=7.9Hz)<br>13.15~13.75(1H, broad) | 3305 (KBr)<br>2937<br>1728<br>1636<br>1576<br>1452<br>1332<br>1266<br>1220<br>1153<br>993<br>895 |

Following the procedure and reaction conditions disclosed in Example 1c using Compounds 1b–13b in Table 3, there were obtained the corresponding compounds shown in Table 4.

TABLE 4

$$R^1NOC\underset{H}{\overset{O}{\phantom{|}}}\overset{\phantom{|}}{\underset{H}{CON}}-\overset{\phantom{|}}{\underset{CH_2CH_3}{\underset{|}{\underset{CHCH_3}{\underset{|}{CH}}}}}-CON-\underset{\phantom{|}}{CO_2CH_2}-\phantom{|}\text{Ph}$$

| Compound No. | $R^1$ | NMR (DMSO-$d_6$) δ(ppm) | IR(cm$^{-1}$) | MS(FAB) (M/Z) |
|---|---|---|---|---|
| 2c | $CH_3CH_2-$ | 0.79(3H, t, J=7.3Hz)<br>0.86(3H, d, J=6.9Hz)<br>0.96~1.22(1H, m)<br>1.02(3H, t, J=7.2Hz)<br>1.36~1.60(1H, m)<br>1.68~2.32(5H, m)<br>3.11(2H, dq, J=5.7, 7.2Hz)<br>3.45(1H, d, J=1.8Hz)<br>3.53~3.85(2H, m)<br>3.65(1H, d, J=1.8Hz)<br>4.35~4.48(2H, m)<br>5.12(2H, s)<br>7.36(5H, s)<br>8.35(1H, t, J=5.7Hz)<br>8.77(1H, d, J=8.6Hz) | (KBr)<br>3292<br>2970<br>1746<br>1630<br>1546<br>1453<br>1273<br>1171<br>894 | 460(MH$^+$) |
| 3c | $(CH_3)_2CH-$ | 0.79(3H, t, J=7.4Hz)<br>0.89(3H, d, J=6.8Hz)<br>0.95~1.25(1H, m)<br>1.07(6H, d, J=6.6Hz)<br>1.33-1.63(1H, m)<br>1.65~2.28(5H, m)<br>3.45(1H, d, J=1.8Hz)<br>3.52~3.98(3H, m)<br>3.65(1H, d, J=1.8Hz)<br>4.33~4.48(2H, m)<br>5.12(2H, s)<br>7.36(5H, s)<br>8.26(1H, d, J=7.7Hz)<br>8.73(1H, d, J=8.4Hz) | (KBr)<br>3282<br>2971<br>1747<br>1630<br>1541<br>1456<br>1277<br>1172<br>896 | 474(MH$^+$) |
| 4c | $(CH_3)_3C-$ | 0.79(3H, t, J=7.4Hz)<br>0.86(3H, d, J=6.7Hz)<br>0.96~1.20(1H, m)<br>1.26(9H, s)<br>1.36~1.60(1H, m)<br>1.65~2.00(4H, m)<br>2.10~2.28(1H, m)<br>3.49(1H, d, J=1.8Hz)<br>3.53~3.68(1H, m)<br>3.63(1H, d, J=1.8Hz)<br>3.71~3.85(1H, m)<br>4.35~4.47(1H, m)<br>5.11(2H, s)<br>7.36(5H, s)<br>8.03(1H, bs)<br>8.72(1H, d, J=8.4Hz) | (KBr)<br>3282<br>2969<br>1747<br>1687<br>1630<br>1535<br>1455<br>1365<br>1278<br>1216<br>1170<br>894 | 488(MH$^+$) |
| 5c | $(CH_3)_2CHCH_2-$ | 0.74~0.96(12H, m)<br>0.97~1.20(1H, m)<br>1.37~1.57(1H, m)<br>1.59~2.00(5H, m)<br>2.09~2.30(1H, m)<br>2.77~3.06(2H, m)<br>3.51(1H, d, J=1.8Hz)<br>3.54~3.69(1H, m)<br>3.66(1H, d, J=1.8Hz)<br>3.71~3.85(1H, m)<br>4.34~5.00(2H, m)<br>5.12(2H, s)<br>7.36(5H, s)<br>8.32(1H, t, J=6.0Hz)<br>8.78(1H, d, J=8.4Hz) | (KBr)<br>3289<br>2963<br>1747<br>1631<br>1541<br>1455<br>1386<br>1352<br>1276<br>1171<br>900 | 488(MH$^+$) |
| 6c | $CH_3(CH_2)_3-$ | 0.79(3H, t, J=7.3Hz)<br>0.85(3H, d, J=6.8Hz)<br>0.86(3H, t, J=6.8Hz)<br>0.95~1.60(6H, m)<br>1.66~2.02(4H, m)<br>2.10~2.30(1H, m)<br>2.98~3.18(2H, m)<br>3.47(1H, d, J=1.8Hz)<br>3.53~3.69(1H, m)<br>3.65(1H, d, J=1.8Hz)<br>3.70~3.85(1H, m) | (CHCl$_3$)<br>3416<br>3013<br>2966<br>1742<br>1684<br>1642<br>1520<br>1448<br>1384<br>1353 | 488(MH$^+$) |

TABLE 4-continued

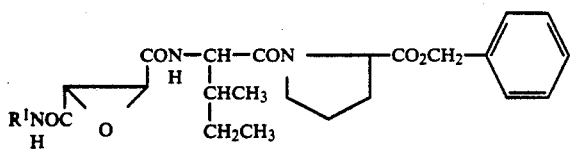

| Compound No. | R¹ | NMR (DMSO-d₆) δ(ppm) | IR(cm⁻¹) | MS(FAB) (M/Z) |
|---|---|---|---|---|
| | | 4.30~4.50(2H, m) | 1276 | |
| | | 5.12(2H, s) | 1237 | |
| | | 7.36(5H, s) | 1174 | |
| | | 8.31(1H, t, J=5.6Hz) | 1107 | |
| | | 8.76(1H, d, J=8.5Hz) | 897 | |
| 7c | $(CH_3)_2CH(CH_2)_2-$ | 0.72~0.93(12H, m) | $(CHCl_3)$ | 502(MH⁺) |
| | | 0.94~1.20(1H, m) | 3415 | |
| | | 1.23~1.37(2H, m) | 3013 | |
| | | 1.38~1.66(2H, m) | 2964 | |
| | | 1.68~2.02(4H, m) | 1742 | |
| | | 2.10~2.30(1H, m) | 1684 | |
| | | 3.00~3.20(2H, m) | 1645 | |
| | | 3.46(1H, d, J=1.8Hz) | 1520 | |
| | | 3.50~3.69(1H, m) | 1447 | |
| | | 3.64(1H, d, J=1.8Hz) | 1237 | |
| | | 3.70~3.86(1H, m) | 1173 | |
| | | 4.35~4.48(2H, m) | 1107 | |
| | | 5.12(2H, s) | 896 | |
| | | 7.36(5H, s) | | |
| | | 8.29(1H, t, J=5.7Hz) | | |
| | | 8.76(1H, d, J=8.4Hz) | | |
| 8c | $CH_3(CH_2)_4-$ | 0.80(3H, t, J=7.3Hz) | $(CHCl_3)$ | 502(MH⁺) |
| | | 0.85(3H, d, J=6.8Hz) | 3416 | |
| | | 0.86(3H, t, J=6.4Hz) | 3012 | |
| | | 0.98~1.59(8H, m) | 2965 | |
| | | 1.67~2.02(4H, m) | 1743 | |
| | | 2.10~2.28(1H, m) | 1685 | |
| | | 2.97~3.17(2H, m) | 1645 | |
| | | 3.47(1H, d, J=1.8Hz) | 1520 | |
| | | 3.54~3.69(1H, m) | 1446 | |
| | | 3.65(1H, d, J=1.8Hz) | 1384 | |
| | | 3.70~3.86(1H, m) | 1353 | |
| | | 4.34~4.50(2H, m) | 1237 | |
| | | 5.12(2H, s) | 1174 | |
| | | 7.36(5H, s) | 1107 | |
| | | 8.32(1H, t, J=5.7Hz) | 898 | |
| | | 8.76(1H, d, J=8.5Hz) | | |
| 9c | $CH_3(CH_2)_5-$ | 0.80(3H, t, J=7.2Hz) | $(CHCl_3)$ | 516(MH⁺) |
| | | 0.85(3H, d, J=6.9Hz) | 3416 | |
| | | 0.86(3H, t, J=6.0Hz) | 2965 | |
| | | 0.95~1.60(10H, m) | 2933 | |
| | | 1.65~2.02(4H, m) | 1742 | |
| | | 2.10~2.30(1H, m) | 1685 | |
| | | 3.00~3.15(2H, m) | 1645 | |
| | | 3.47(1H, d, J=1.8Hz) | 1520 | |
| | | 3.52~3.69(1H, m) | 1446 | |
| | | 3.64(1H, d, J=1.8Hz) | 1238 | |
| | | 3.70~3.85(1H, m) | 1173 | |
| | | 4.34~4.50(2H, m) | 1107 | |
| | | 5.12(2H, s) | 898 | |
| | | 7.36(5H, s) | | |
| | | 8.32(1H, t, J=5.9Hz) | | |
| | | 8.75(1H, d, J=8.2Hz) | | |
| 10c | $CH_3(CH_2)_6-$ | 0.80(3H, t, J=7.3Hz) | $(CHCl_3)$ | 530(MH⁺) |
| | | 0.86(3H, d, J=6.8Hz) | 3417 | |
| | | 0.86(3H, t, J=5.6Hz) | 3013 | |
| | | 0.95~1.60(12H, m) | 2964 | |
| | | 1.65~2.02(4H, m) | 2932 | |
| | | 2.10~2.28(1H, m) | 1742 | |
| | | 2.98~3.16(2H, m) | 1685 | |
| | | 3.47(1H, d, J=1.8Hz) | 1645 | |
| | | 3.52~3.69(1H, m) | 1520 | |
| | | 3.64(1H, d, J=1.8Hz) | 1446 | |
| | | 3.70~3.85(1H, m) | 1237 | |
| | | 4.34~4.51(2H, m) | 1107 | |
| | | 5.12(2H, s) | 897 | |
| | | 7.36(5H, s) | | |
| | | 8.32(1H, t, J=5.6Hz) | | |
| | | 8.75(1H, d, J=8.4Hz) | | |
| 11c | $PhCH_2-$ | 0.80(3H, t, J=7.4Hz) | (KBr) | 522(MH⁺) |
| | | 0.86(3H, d, J=6.8Hz) | 3286 | |
| | | 0.95~1.25(1H, m) | 2966 | |

TABLE 4-continued $$\text{R}^1\text{NOCH-}\underset{\text{O}}{\triangle}\text{-CON-CH-CON-}\underset{\underset{\text{CH}_2\text{CH}_3}{|}}{\overset{\overset{\text{H}}{|}}{\text{CHCH}_3}}\text{-}\bigg\langle\bigg\rangle\text{-CO}_2\text{CH}_2\text{-}\text{Ph}$$

| Compound No. | $R^1$ | NMR (DMSO-$d_6$) $\delta$(ppm) | IR(cm$^{-1}$) | MS(FAB) (M/Z) |
|---|---|---|---|---|
| | | 1.36~1.60(1H, m) | 1746 | |
| | | 1.65~2.03(4H, m) | 1679 | |
| | | 2.10~2.30(1H, m) | 1628 | |
| | | 3.55(1H, d, J=1.8Hz) | 1536 | |
| | | 3.56~3.69(1H, m) | 1455 | |
| | | 3.71(1H, d, J=1.8Hz) | 1384 | |
| | | 3.72~3.86(1H, m) | 1352 | |
| | | 4.20~4.50(4H, m) | 1276 | |
| | | 5.13(2H, s) | 1170 | |
| | | 7.20~7.50(10H, m) | 1096 | |
| | | 8.80(1H, t, J=8.4Hz) | 1029 | |
| | | 8.88(1H, t, J=5.9Hz) | 899 | |
| 12c | Ph— | 0.81(3H, t, J=7.5Hz) | (KBr) | 508(MH$^+$) |
| | | 0.87(3H, d, J=6.8Hz) | 3279 | |
| | | 0.97~1.25(1H, m) | 2965 | |
| | | 1.38~1.63(1H, m) | 1746 | |
| | | 1.67~1.98(4H, m) | 1693 | |
| | | 2.09~2.30(1H, m) | 1626 | |
| | | 3.54~3.88(2H, m) | 1537 | |
| | | 3.72(1H, d, J=1.7Hz) | 1446 | |
| | | 3.79(1H, d, J=1.7Hz) | 1168 | |
| | | 4.33~4.55(2H, m) | 895 | |
| | | 5.12(2H, s) | | |
| | | 7.02~7.16(1H, m) | | |
| | | 7.20~7.50(7H, m) | | |
| | | 7.55~7.70(2H, m) | | |
| | | 8.82(1H, d, J=8.5Hz) | | |
| | | 10.45(1H, s) | | |
| 13c | $C_6H_{11}$— | 0.80(3H, t, J=7.3Hz) | (KBr) | 514(MH$^+$) |
| | | 0.87(3H, d, J=6.8Hz) | 3283 | |
| | | 0.96~1.97(16H, m) | 2933 | |
| | | 2.09~2.30(1H, m) | 2856 | |
| | | 3.48(1H, d, J=1.7Hz) | 1747 | |
| | | 3.51~3.64(2H, m) | 1631 | |
| | | 3.65(1H, d, J=1.7Hz) | 1536 | |
| | | 3.70~3.86(1H, m) | 1452 | |
| | | 4.35~4.49(2H, m) | 898 | |
| | | 5.12(2H, s) | | |
| | | 7.36(5H, s) | | |
| | | 8.30(1H, d, J=7.9Hz) | | |
| | | 8.76(1H, d, J=8.6Hz) | | |

Following the procedure and reaction conditions disclosed in Example 1d using Compounds 2c–13c in Table 3, there were obtained the corresponding compounds shown in Table 5.

TABLE 5

$$\text{R}^1\text{NOCH-}\underset{\text{O}}{\triangle}\text{-CON-CH-CON-}\underset{\underset{\text{CH}_2\text{CH}_3}{|}}{\overset{\overset{\text{H}}{|}}{\text{CHCH}_3}}\text{-}\bigg\langle\bigg\rangle\text{-CO}_2\text{H}$$

| Compound No. | $R^1$ | NMR (DMSO-$d_6$) $\delta$(ppm) | IR(cm$^{-1}$) | MS(FAB) (M/Z) |
|---|---|---|---|---|
| 2d | $CH_3CH_2$— | 0.83(3H, t, J=7.2Hz) | (KBr) | 370(MH$^+$) |
| | | 0.92(3H, d, J=6.8Hz) | 3286 | |
| | | 0.95~1.25(1H, m) | 2971 | |
| | | 1.02(3H, t, J=7.1Hz) | 1739 | |
| | | 1.38~1.62(1H, m) | 1631 | |
| | | 1.65~2.30(5H, m) | 1541 | |
| | | 3.14(2H, dq, J=5.6, 7.1Hz) | 1451 | |
| | | 3.45(1H, d, J=1.8Hz) | 1190 | |
| | | 3.50~3.85(2H, m) | 894 | |
| | | 3.65(1H, d, J=1.8Hz) | | |
| | | 4.20~4.31(1H, m) | | |
| | | 4.42(1H, dd, J=8.5, 8.5Hz) | | |
| | | 8.35(1H, t, J=5.6Hz) | | |

TABLE 5-continued $$\text{R}^1\text{NOCH} \underset{\text{O}}{\overset{}{\diagdown}} \text{CON}\underset{\text{H}}{\overset{}{-}}\text{CH}\underset{\overset{|}{\text{CHCH}_3}}{\overset{}{-}}\text{CON} \diagdown \text{CO}_2\text{H}$$
$$\overset{}{\underset{\text{CH}_2\text{CH}_3}{}}$$

| Compound No. | R¹ | NMR (DMSO-d₆) δ(ppm) | IR(cm⁻¹) | MS(FAB) (M/Z) |
|---|---|---|---|---|
| | | 8.72(1H, d, J=8.5Hz)<br>12.20~12.80(1H, broad) | | |
| 3d | (CH₃)₂CH— | 0.83(3H, t, J=7.3Hz)<br>0.92(3H, d, J=6.8Hz)<br>1.00~1.30(1H, m)<br>1.07(6H, d, J=6.6Hz)<br>1.35~1.63(1H, m)<br>1.65~2.25(5H, m)<br>3.45(1H, d, J=1.8Hz)<br>3.50~3.96(3H, m)<br>3.65(1H, d, J=1.8Hz)<br>4.20~4.30(1H, m)<br>4.41(1H, dd, J=8.5, 8.5Hz)<br>8.27(1H, d, J=7.6Hz)<br>8.71(1H, d, J=8.5Hz)<br>12.30~12.75(1H, broad) | (KBr)<br>3283<br>2973<br>1738<br>1630<br>1545<br>1453<br>1370<br>1242<br>1191<br>897 | 384(MH⁺) |
| 4d | (CH₃)₃C— | 0.83(3H, t, J=7.3Hz)<br>0.92(3H, d, J=6.7Hz)<br>0.95~1.25(1H, m)<br>1.27(9H, s)<br>1.40~1.62(1H, m)<br>1.68~2.03(4H, m)<br>2.05~2.22(1H, m)<br>3.49(1H, d, J=1.8Hz)<br>3.52~3.68(1H, m)<br>3.63(1H, d, J=1.8Hz)<br>3.69~3.83(1H, m)<br>4.18~4.29(1H, m)<br>4.41(1H, dd, J=8.4, 8.4Hz)<br>8.03(1H, s)<br>8.69(1H, d, J=8.4Hz)<br>12.35~12.65(1H, broad) | (KBr)<br>3304<br>2970<br>1739<br>1631<br>1536<br>1455<br>1395<br>1367<br>1323<br>1222<br>1190<br>895 | 398(MH⁺) |
| 5d | (CH₃)₂CHCH₂— | 0.83(3H, t, J=6.9Hz)<br>0.84(6H, d, J=6.8Hz)<br>0.92(3H, d, J=6.6Hz)<br>0.98~1.24(1H, m)<br>1.38~1.60(1H, m)<br>1.60~2.02(5H, m)<br>2.03~2.25(1H, m)<br>2.79~3.05(2H, m)<br>3.51(1H, d, J=1.8Hz)<br>3.52~3.68(1H, m)<br>3.66(1H, d, J=1.8Hz)<br>3.68~3.83(1H, m)<br>4.20~4.30(1H, m)<br>4.43(1H, dd, J=8.5, 8.5Hz)<br>8.33(1H, t, J=6.0Hz)<br>8.76(1H, d, J=8.5Hz)<br>12.25~12.75(1H, broad) | (KBr)<br>3286<br>2965<br>1738<br>1630<br>1543<br>1452<br>1190<br>900 | 398(MH⁺) |
| 6d | CH₃(CH₂)₃— | 0.80~1.02(9H, m)<br>1.03~1.66(6H, m)<br>1.70~2.07(4H, m)<br>2.08~2.32(1H, m)<br>3.00~3.23(2H, m)<br>3.52(1H, d, J=1.8Hz)<br>3.56~3.88(2H, m)<br>3.70(1H, d, J=1.8Hz)<br>4.24~4.35(1H, m)<br>4.47(1H, dd, J=8.5, 8.5Hz)<br>8.36(1H, t, J=5.7Hz)<br>8.79(1H, d, J=8.5Hz)<br>12.35~12.80(1H, broad) | (KBr)<br>3284<br>2964<br>1739<br>1628<br>1542<br>1452<br>1321<br>1226<br>1190<br>895 | 398(MH⁺) |
| 7d | (CH₃)₂CH(CH₂)₂— | 0.83(3H, t, J=7.4Hz)<br>0.86(6H, d, J=6.6Hz)<br>0.92(3H, d, J=6.8Hz)<br>0.98~1.20(1H, m)<br>1.23~1.38(2H, m)<br>1.40~1.67(2H, m)<br>1.68~2.02(4H, m)<br>2.05~2.24(1H, m) | (KBr)<br>3287<br>2962<br>1739<br>1631<br>1541<br>1453<br>1386 | 412(MH⁺) |

TABLE 5-continued

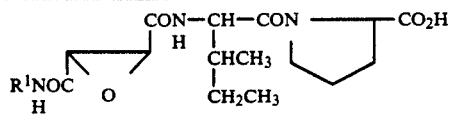

| Compound No. | $R^1$ | NMR (DMSO-$d_6$) δ(ppm) | IR(cm$^{-1}$) | MS(FAB) (M/Z) |
|---|---|---|---|---|
| | | 3.00~3.21(2H, m) | 1227 | |
| | | 3.46(1H, d, J=1.8Hz) | 1189 | |
| | | 3.52~3.68(1H, m) | 895 | |
| | | 3.64(1H, d, J=1.8Hz) | | |
| | | 3.68~3.83(1H, m) | | |
| | | 4.20~4.30(1H, m) | | |
| | | 4.42(1H, dd, J=8.4, 8.6Hz) | | |
| | | 8.30(1H, t, J=5.8Hz) | | |
| | | 8.74(1H, d, J=8.4Hz) | | |
| | | 12.35~12.65(1H, broad) | | |
| 8d | $CH_3(CH_2)_4-$ | 0.83(3H, t, J=6.9Hz) | (KBr) | 412(MH$^+$) |
| | | 0.86(3H, t, J=6.7Hz) | 3286 | |
| | | 0.92(3H, d, J=6.8Hz) | 2963 | |
| | | 0.98~1.63(8H, m) | 2934 | |
| | | 1.65~2.03(4H, m) | 1740 | |
| | | 2.05~2.25(1H, m) | 1628 | |
| | | 2.93~3.15(2H, m) | 1541 | |
| | | 3.47(1H, d, J=1.8Hz) | 1454 | |
| | | 3.55~3.84(2H, m) | 1322 | |
| | | 3.65(1H, d, J=1.8Hz) | 1190 | |
| | | 4.20~4.25(1H, m) | 897 | |
| | | 4.42(1H, dd, J=8.6, 8.6Hz) | | |
| | | 8.32(1H, t, J=5.6Hz) | | |
| | | 8.72(1H, d, J=8.6Hz) | | |
| | | 12.30~12.80(1H, broad) | | |
| 9d | $CH_3(CH_2)_5-$ | 0.83(3H, t, J=6.8Hz) | (KBr) | 426(MH$^+$) |
| | | 0.86(3H, t, J=6.5Hz) | 3284 | |
| | | 0.92(3H, d, J=6.8Hz) | 2962 | |
| | | 0.98~1.62(10H, m) | 2933 | |
| | | 1.67~2.02(4H, m) | 1739 | |
| | | 2.06~2.25(1H, m) | 1629 | |
| | | 3.00~3.14(2H, m) | 1542 | |
| | | 3.47(1H, d, J=1.8Hz) | 1454 | |
| | | 3.52~3.68(1H, m) | 1322 | |
| | | 3.64(1H, d, J=1.8Hz) | 1191 | |
| | | 3.69~3.84(1H, m) | 898 | |
| | | 4.19~4.30(1H, m) | | |
| | | 4.42(1H, dd, J=8.4, 8.6Hz) | | |
| | | 8.33(1H, t, J=5.6Hz) | | |
| | | 8.73(1H, d, J=8.4Hz) | | |
| | | 12.30~12.75(1H, broad) | | |
| 10d | $CH_3(CH_2)_6-$ | 0.83(3H, t, J=6.7Hz) | (KBr) | 440(MH$^+$) |
| | | 0.86(3H, t, J=6.5Hz) | 3285 | |
| | | 0.92(3H, d, J=6.8Hz) | 2962 | |
| | | 0.97~1.62(12H, m) | 2931 | |
| | | 1.67~2.00(4H, m) | 1743 | |
| | | 2.06~2.26(1H, m) | 1628 | |
| | | 2.97~3.15(2H, m) | 1542 | |
| | | 3.47(1H, d, J=1.8Hz) | 1455 | |
| | | 3.52~3.68(1H, m) | 1322 | |
| | | 3.64(1H, d, J=1.8Hz) | 1189 | |
| | | 3.68~3.83(1H, m) | 896 | |
| | | 4.20~4.31(1H, m) | | |
| | | 4.42(1H, dd, J=8.6, 8.6Hz) | | |
| | | 8.32(1H, t, J=5.6Hz) | | |
| | | 8.73(1H, d, J=8.6Hz) | | |
| | | 12.35~12.70(1H, broad) | | |
| 11d | $PhCH_2-$ | 0.83(3H, t, J=7.3Hz) | (KBr) | 432(MH$^+$) |
| | | 0.92(3H, d, J=6.6Hz) | 3286 | |
| | | 0.95~1.28(1H, m) | 2968 | |
| | | 1.38~1.63(1H, m) | 1739 | |
| | | 1.65~2.03(4H, m) | 1627 | |
| | | 2.07~2.24(1H, m) | 1537 | |
| | | 3.50~3.66(1H, m) | 1455 | |
| | | 3.55(1H, d, J=1.9Hz) | 1323 | |
| | | 3.68~3.85(1H, m) | 1227 | |
| | | 3.71(1H, d, J=1.9Hz) | 1189 | |
| | | 4.15~4.50(4H, m) | 898 | |
| | | 7.20~7.40(5H, m) | | |
| | | 8.75(1H, d, J=8.4Hz) | | |

TABLE 5-continued $$\text{R}^1\text{NOCH} \diagup\!\!\!\!\diagdown_O \diagup\!\!\!\!\diagdown \text{CON}\!-\!\text{CH}\!-\!\text{CON} \diagup\!\!\!\!\diagdown \text{CO}_2\text{H}$$
with H, CHCH$_3$, CH$_2$CH$_3$

| Compound No. | R$^1$ | NMR (DMSO-d$_6$) δ(ppm) | IR(cm$^{-1}$) | MS(FAB) (M/Z) |
|---|---|---|---|---|
| 12d | Ph— | 8.87(1H, t, J=5.9Hz)<br>12.30~12.80(1H, broad)<br>0.85(3H, t, J=7.3Hz)<br>0.94(3H, d, J=6.6Hz)<br>0.97~1.30(1H, m)<br>1.41~1.64(1H, m)<br>1.64~2.02(4H, m)<br>2.04~2.24(1H, m)<br>3.50~3.90(2H, m)<br>3.73(1H, d, J=1.7Hz)<br>3.79(1H, d, J=1.7Hz)<br>4.17~4.32(1H, m)<br>4.35~4.54(1H, m)<br>7.02~7.16(1H, m)<br>7.24~7.40(2H, m)<br>7.54~7.70(2H, m)<br>8.82(1H, d, J=8.4Hz)<br>10.42(1H, s) | (KBr)<br>3338<br>3274<br>2969<br>1697<br>1674<br>1619<br>1548<br>1447<br>1190<br>897 | 418(MH$^+$) |
| 13d | C$_6$H$_{11}$— | 12.25~12.75(1H, broad)<br>0.82(3H, t, J=7.2Hz)<br>0.94(3H, d, J=6.6Hz)<br>1.06~2.02(16H, m)<br>2.05~2.24(1H, m)<br>3.48(1H, d, J=1.7Hz)<br>3.50~3.63(2H, m)<br>3.65(1H, d, J=1.7Hz)<br>3.67~3.86(1H, m)<br>4.20~4.30(1H, m)<br>4.30~4.49(1H, m)<br>8.31(1H, d, J=7.9Hz)<br>8.75(1H, d, J=8.4Hz)<br>12.30~12.75(1H, broad) | (KBr)<br>3291<br>2934<br>2857<br>1743<br>1631<br>1537<br>1451<br>894 | 424(MH$^+$) |

INDUSTRIAL UTILIZATION

For use of the compounds of Formula I for the treatment of muscular atrophy diseases, the compounds of the present invention are administered orally or parenterally in the dosage form of tablets, pills, capsules, granules and injectional solutions. These preparations can be prepared according to the conventional practices using ordinary additives such as fillers, binders, disintegrators, pH adjusting agents and solubilizers.

The dosage of the compound of Formula I for therapy to a patient depends on the age of the patient and kind and conditions of the diseases, but usually it is in the range from 10 to 2000 mg in single or several divided doses per day.

We claim:

1. An epoxysuccinamic acid derivative represented by the formula:

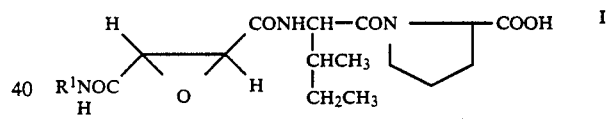

wherein R$^1$ is an alkyl group having 1 to 10 carbon atoms, a phenyl group or a benzyl group or a pharmaceutically acceptable salt thereof.

2. An epoxysuccinamic acid derivative according to claim 1 wherein the compound of Formula I is N-(L-3-trans-n-propylcarbamoyloxirane-2-carbonyl)-L-isoleucyl-L-proline.

3. An epoxysuccinamic acid derivative according to claim 1 wherein the compound of Formula I is N-(L-3-trans-n-pentylcarbamoyloxirane-2-carbonyl)-L-isoleucyl-L-proline.

4. An epoxysuccinamic acid derivative represented by the formula:

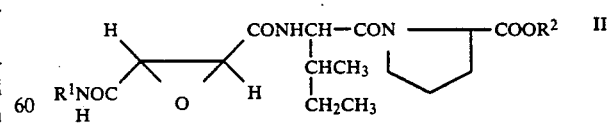

wherein R$^1$ is an alkyl group having 1 to 10 carbon atoms, a phenyl group or a benzyl group, and R$^2$ is a protecting group of the carboxyl group.

* * * * *